(12) United States Patent
Bird

(10) Patent No.: US 8,957,099 B2
(45) Date of Patent: Feb. 17, 2015

(54) TREATMENT OF ADHD

(75) Inventor: Philip Bird, Maroochydore (AU)

(73) Assignee: Gosforth Centre (Holdings) Pty Ltd., Maroochydore, Queensland (AU)

(*) Notice: Subject to any disclaimer, the term of this patent is extended or adjusted under 35 U.S.C. 154(b) by 895 days.

(21) Appl. No.: 12/526,191

(22) PCT Filed: Feb. 7, 2008

(86) PCT No.: PCT/AU2008/000154
§ 371 (c)(1),
(2), (4) Date: Oct. 20, 2009

(87) PCT Pub. No.: WO2008/095253
PCT Pub. Date: Aug. 14, 2008

(65) Prior Publication Data
US 2010/0087422 A1    Apr. 8, 2010

Related U.S. Application Data

(63) Continuation-in-part of application No. PCT/AU2007/000421, filed on Mar. 30, 2007.

(60) Provisional application No. 60/900,043, filed on Feb. 7, 2007.

(51) Int. Cl.
*A61K 31/4166* (2006.01)
*A61K 31/19* (2006.01)
*A61K 31/195* (2006.01)
*A61K 31/35* (2006.01)
*A61K 31/445* (2006.01)
*A61K 31/4458* (2006.01)
*A61K 31/53* (2006.01)
*A61K 31/55* (2006.01)

(52) U.S. Cl.
CPC .............. *A61K 31/19* (2013.01); *A61K 31/4166* (2013.01); *A61K 31/195* (2013.01); *A61K 31/35* (2013.01); *A61K 31/445* (2013.01); *A61K 31/4458* (2013.01); *A61K 31/53* (2013.01); *A61K 31/55* (2013.01)
USPC ........................................................ 514/391

(58) Field of Classification Search
CPC .................................................. A61K 31/4166
USPC ......... 514/217, 317, 326, 376, 386, 391, 455, 514/557, 561
See application file for complete search history.

(56) References Cited

U.S. PATENT DOCUMENTS

| | | |
|---|---|---|
| 2002/0058656 A1 | 5/2002 | Ockert |
| 2003/0060423 A1 | 3/2003 | Plata-Salaman |
| 2004/0258758 A1 | 12/2004 | Gustow et al. |
| 2006/0052428 A1* | 3/2006 | Chez ............................ 514/396 |
| 2011/0065628 A1 | 3/2011 | Johnson et al. |
| 2011/0207718 A1 | 8/2011 | Bird |

FOREIGN PATENT DOCUMENTS

| | | |
|---|---|---|
| EP | 1 600 167 A2 | 11/2005 |
| WO | WO 93/21910 A1 | 11/1993 |
| WO | WO 01/39779 A1 | 6/2001 |
| WO | WO 03/013514 A1 | 2/2003 |
| WO | WO 03/030899 A2 | 4/2003 |
| WO | 2004002462 | 1/2004 |
| WO | WO 2006/120501 A1 | 11/2006 |
| WO | WO 2008/095221 A1 | 8/2008 |
| WO | WO 2009/014762 A1 | 1/2009 |
| WO | WO 2009/139901 A2 | 11/2009 |
| WO | WO 2010/015029 A1 | 2/2010 |
| WO | WO 2011/100373 A1 | 8/2011 |
| WO | WO 2011/143721 A1 | 11/2011 |

OTHER PUBLICATIONS

Schaller et al., "Carbamazepine and methylphenidate in ADHD," Journal of the American Academy of Child and Adolescent Psychiatry, 38:2, Feb. 1999, pp. 112-113.
EPO, Supplementary European Search Report for European application No. EP08700447, Munich, Germany, Mar. 11, 2010.
Frank, "Visual Event Related Potentials After Methylphenidate and Sodium Valproate in Children with Attention Deficit Hyperactivity Disorder," Clinical Electroencephalography, 1993, pp. 19-24, vol. 24, No. 1.
Hamrin et al., "Gabapentin and Methylphenidate Treatment of a Preadolescent with Attention Deficit Hyperactivity Disorder and Bipolar Disorder," Journal of Child and Adolescent Pychopharmacology, 2001, pp. 301-09, vol. 11, No. 3.
Schreier, "Risperidone for Young Children with Mood Disorders and Aggressive Behavior," Journal of Child and Adolescent Pychopharmacology, 1998, pp. 49-59, vol. 8, No. 1.

(Continued)

*Primary Examiner* — Jennifer M Kim
(74) *Attorney, Agent, or Firm* — Leydig, Voit & Mayer, Ltd.

(57) ABSTRACT

A method is described for treating attention deficit hyperactivity disorder (ADHD), by administering to the individual an anti-epileptic mood stabilizer at a dose which is sub-therapeutic for mood stabilization, optionally in combination with a psychostimulant. Also described is a method of improving reading comprehension and/or fluency in an individual suffering from learning difficulties which method comprises administering to the individual an anti-epileptic mood stabilizer.

2 Claims, No Drawings

(56) References Cited

OTHER PUBLICATIONS

Davids et al., "A pilot clinical trial of oxcarbazepine in adults with attention deficit hyperactivity disorder," Progress in Neuro-Psychopharmacology & Biological Psychiatry, 2006, pp. 1033-1038, vol. 30.
Baskys et al., *Drug Development Research*, 56: 393-400 (2002).
Bernejo, *Movement Disorders*, 22(14): (2007).
Chiu et al., *Psychiatry and Clinical Neurosciences*, 61: 630-633 (2007).
Dhikav, *Medical Hypotheses* 67: 725-728 (2006).
Grunze, *Dialogues Clin Neurosci.*, 10: 77-89 (2008).
Hill, *Movement Disorders*, 18(11): 1301-1371 (2003).
Miyazaki et al., *Brain and Development*, 28: 470-472 (2006).
Reis et al. *Bras Psiquiatr.*, 30(2): 132-135 (2008).
Rogawski, Nature Medicine, 10(7), (Jul. 2004).
Scheffer et al., *Am. J. Psychiatry*, 162(1): 58-64 (Jan. 2005).
Silva et al., *J. Am. Acad. Child Adolesc. Psychiatry*, 35(3): 352-358 (Mar. 1996).
Yitzchak, *Clinical Electroencephalography*, 24(1): 19-24 (1993).
Zaremba et al., *Pharmacological Reports*, 58: 1-12 (2008).
Australian Patent Office, International Search Report in International Application No. PCT/AU2009/001000 (Oct. 6, 2009).
Australian Patent Office, International Search Report in International Application No. PCT/AU2008/000154 (Jun. 10, 2009).
Australian Patent Office, International Search Report in International Application No. PCT/AU2007/00421 (Jun. 29, 2007).
United Kingdom Patent Office, Search Report in GB Patent Application No. 1111712.4 (Oct. 11, 2011).
United Kingdom Patent Office, Search Report in GB Patent Application No. 1111712.4 (Feb. 10, 2012).
Loy et al., *Journal of Molecular Neuroscience*, 19: 303-307 (2002).
Tekin et al., *Journal of Neural Transmission*, 105: 295-303 (1998).

\* cited by examiner

TREATMENT OF ADHD

FIELD AND BACKGROUND TO THE INVENTION

The present invention relates to the treatment of individuals with attention-deficit hyperactivity disorder with an anti-epileptic mood stabiliser (AEDMS), optionally in combination with psychostimulants, for example to improve psychosocial and cognitive function in such individuals. The present invention also relates to the treatment of individuals with other DSM-IV-TR classified disorders, such as autistic spectrum disorders. The present invention further relates to the treatment of learning difficulties, such as reading difficulties.

Attention-deficit hyperactivity disorder (ADHD) is a developmental disorder distinguished by symptoms of inattention, hyperactivity and impulsivity (Snyder, Nussbaum, & Robins (Eds.), 2006, Clinical Neuropsychology: A Pocket Handbook for Assessment, APABooks, Washington D.C.). Although ADHD is one of the most frequently diagnosed psychological disorders in childhood long-term studies have demonstrated that symptoms can be maintained into adulthood. The number of children and adolescents who maintain ADHD symptoms and continue their treatment as adults ranges from 36% to 65%. Data derived from longitudinal studies suggest that although the symptom cluster of hyperactivity and impulsivity decays over time, the symptoms of inattention persist and the proportion of clinically referred adults with ADHD endorsing prominent inattentive symptoms may be as high as 90%. Adult ADHD has now been recognised as a valid clinical entity that is associated with profound psychosocial and cognitive impairments (Weiss & Murray, 2003, CMAJ. 168(6): 715-22).

Studies of children and adults with ADHD indicate that many experience an array of cognitive impairments that extend beyond the behavioural symptoms outlined in the diagnostic criteria for the disorder (DSM-IV-TR; American Psychiatric Association, 2000). Higher level cognitive and information processing impairments have been reported, the functional day-to-day implications of which include chronic difficulties in maintaining alertness, self-discipline, establishing and keeping routines, and completing tasks. Adults with ADHD change jobs more often, accrue more speeding tickets and have more vehicle accidents than adults without the disorder.

It is well established that ADHD can occur with learning disorders (LD) in children at a rate substantially above chance levels, typically ranging between 25% and 40%. It is also becoming evident that for both ADHD and LD the underlying cognitive impairments seem to persist in a life span perspective. One recent study has examined the co-morbidity between ADHD and LD in an adult population. Samuelsson et al., 2004 (J. Learn. Disabil. 37(2):155-68) found no differences between adults with and without ADHD on measures of either phonological processing skills or word decoding; however adults with ADHD performed significantly worse on tests of reading comprehension than those who did not have ADHD. Samuelsson et al. concluded that the results are consistent with the view that reading comprehension involves many of the higher cognitive control functions thought to be impaired in ADHD.

The primary psychopharmacological agents used to treat ADHD are the CNS stimulants (pyschostimulants). Studies of the short term beneficial effects of stimulants on the symptoms of ADHD constitute the largest body of treatment literature of any childhood-onset psychiatric disorder, with the stimulant medications proven effective across diverse age and diagnostic groups. Until August 2005, the only stimulant available under the Australian Pharmaceutical Benefits Scheme (PBS) was dexamphetamine, explaining its predominant place in Australia for the treatment of ADHD. The PBS has since added methylphenidate to the subsidised listing, the most commonly used CNS stimulant in the US for the treatment of ADHD.

In both children and adolescents, stimulants can provide robust improvement in ADHD behavioural symptoms. Despite this, there is continued functional impairment in patients. In adults this was particularly evident in the area which is often referred to as higher executive function. This includes the ability to sequence, organise and integrate cognitive functioning and appears to be used during the complex interpersonal interaction which forms the basis of human social communication: any impairment in this area is quickly detected by almost every individual although it may not be easily identified or described. The use of stimulant medication enables a reduction in the motivation and effort required to complete a task, but they do not appear to enable the individual to make the complex task easier with repeated exposure. Thus the inevitable fatigue that comes from this is not counterbalanced by improved efficiency and eventually the task is ceased.

This same model can be applied to social interaction. For example, we have noted that the tendency to hyper-focus on a specific topic during conversation did not reduce consistently on stimulants alone, as it would appear that the individual could not process simultaneously the multiple lines of thought that usually take place in normal social interaction. Instead there would be the selection of a preferred more comfortable, possibly more familiar topic and as consequence, resistance to follow the natural flow of the conversation. Thus providing sufficient motivation exists, conversation can occur, but it still requires considerable effort and is often observed by the listener as awkwardness during the interaction and the individual will inevitably, in time, fatigue due to the effort involved. This results in a similar, although delayed, experience of mental exhaustion and failure to sustain attention that existed prior to the commencement of stimulants. Thus, we have observed that unless there is an improvement in the ability to process information, the improved motivation provided by the stimulant will inevitably wane. This is seen clinically with adults with a diagnosis of ADHD treated with stimulants; the initial and at times miraculous improvement frequently gives way to an increasing disorganisation, noncompliance with medication and an eventual ceasing of treatment.

Accordingly, there is a need for an improved treatment for ADHD, which is better, able to reduce the impairment in the underlying cognitive process seen in ADHD patients.

SUMMARY OF THE INVENTION

Sodium Valproate (VPA), a mood stabiliser, is the most widely prescribed anti-epileptic drug worldwide. The pharmacological effects of VPA involve a variety of mechanisms, including gamma-aminobutyric acid (GABA)-ergic transmission, reduced release and/or effects of excitatory amino acids, blockade of voltage-gated sodium channels and modulation dopaminergic and serotoninergic transmission. In addition to its efficacy in treating epilepsy, VPA has also shown to be effective in the treatment of acute mania in six controlled trials, and is now approved in both the USA and Australia for this use.

We have now found that administration of this anti-epileptic mood stabiliser at significantly reduced dosages compared to those used to control epilepsy and stabilise moods (e.g. in individuals suffering from bipolar disorder/manic depression) to individuals suffering from ADHD resulted in a number of unexpected improvements in cognitive and psychosocial functioning. Patients often described their thoughts becoming more manageable and less chaotic. This seemed to allow for more temporal sequencing of ideas, with a resulting overall improvement in psychosocial functioning. These results have subsequently been repeated for a number of other anti-epileptic mood stabilisers when administered at similarly low doses.

Our results indicate that these anti-epileptic drugs exhibit a pharmacological profile at low doses which is fundamentally different from that seen within the anti-epileptic or mood stabilising range. Without wishing to be bound by theory, we believe that the explanation for this is that in low doses the anti-epileptic drugs do not hyperpolarise all neurones across the cerebral cortex but selectively they prolong excitation of those neurones previously excited, thereby improving working memory, whilst having the opposite action on resting potentials of inactive neurons, thereby reducing interference and distractibility. This could be referred as cognitive tuning, cognitive coordination, pacing (i.e. not jumping erratically form one thought to the next), efficient attention shifting (this is the cognitive function whereby one can drift instantaneously from a thought whilst think about something else related and come back to the original thought, this requires the ability to keep thoughts in the back of one's mind without getting lost or losing the thread).

A significant number of patients who reported a subjective improvement in ADHD symptoms also described an improvement in their reading and verbal comprehension abilities. They were more able to attend to the content of both the text and conversation, which was in direct contrast to their previously frustrating experiences of needing to put most of their mental effort into either the process of reading or listening with relatively little comprehension of the content occurring. There is a body of evidence indicating that faulty saccades are a characteristic of individuals who are reading disabled. We have been able to assess oculomotor function using the Developmental Eye Movement Test (DEM): this has shown improvement comparable with that of the patient's own subjective experience of a reduction in the mental effort required to follow written text. Again, these results have been repeated for a number of other anti-epileptic mood stabilisers when administered at low doses. This leads us to the hypothesis that the low dose of the mood stabiliser is having a beneficial effect on fixational and saccade activity during reading and non reading tasks. The magnitude of the change described by many of these individuals was comparable to changes in behaviour that occurred during the initiation of stimulant therapy.

Additionally, the self-reported improvement appeared to correlate closely to notable changes in the complex interpersonal interaction during the clinical consultation. Verbal interactions between the treating psychiatrist and patients appeared more spontaneous and fluid, and patients appeared to be able to provide a higher level of subtle non-verbal feedback during conversations. It would appear, based on this more appropriate non-verbal behaviour, that patients were experiencing a greater understanding of the content as a consequence of less mental effort expended on the process of the conversation. Patients also reported that reading seemed to require less effort, resulting in greater enjoyment in a task that had previously been very cognitively demanding. These tasks which previously could only be maintained for relatively short periods of time without fatigue, could now on the combination of therapy, be sustained in a more effortless, consistent and therefore functionally usable form.

Thus, our clinical observations following augmentation of the stimulant treatment with anti-epileptic mood stabilisers suggested an improvement of the residual cognitive impairment seen with stimulant alone, a frequent and important example being the improved self reliance, organisation and consistence in taking all their prescribed medication. This reduced effort required to consistently remember medication often having a dramatic effect. It was as if at last this activity became automatic instead of the need to continually to allocate mental effort to undertake this simple and repetitive task. Previously, the compliance of medication assessed by pharmacy fill rates even with extended release stimulant formulations was less than 30% after 9 months. By contrast, in our clinic-based sample the combination of a mood stabiliser at low dose and stimulant has improved significantly our patients' adherence to taking all their prescribed medication in comparison to what was previously achieved on stimulant alone.

We have noted benefits in over 90% of those trialled on an anti-epileptic drug (at low doses). In particular the benefits included a subjective improvement in the ability to organise thoughts in conversation with less active effort than was ever previously experienced.

Attention on the content of conversation rather than on the structure. The mental effort was previously expended on just attending to what was being said with little remaining mental available to interpret and then respond appropriately to the content of the conversations It was observed that many of conversational and social adaptations which were previously used, were disregarded, often over a remarkably short time. The changes occurring were often evident between the individuals' weekly appointments. This would suggest that they were therapeutically mediated; by the temporal relationship to the initiation of medication, the apparent effortless nature of the change and also the patients had received no specific instruction on methods to improve their social functioning. With these changes in mind it was remarkable that despite their relative persistence following stabilisation on stimulants they had improved over a very short time period after anti-epileptic drug augmentation.

These positive outcomes are not only initially robust but then continue to improve over time. This pattern is in contrast to our past clinical experience of treating adult with ADHD with stimulants alone, in which considerable effort from that patient the close family and the therapist is required to maintain the early improvement. It has been further noted that there appears no loss in efficacy or tolerance to the medication over the 18 months since the first trials were commenced. In the clinic population it has been further noted that the long term compliance with the combination of a stimulant and the anti-epileptic drug has reliably exceeded that on stimulant alone.

Further studies in our clinic also showed that monotherapy with a low dose of mood stabiliser (no stimulant) also led to many of the significant improvements in the symptoms of ADHD that were seen with the combination therapy.

Thus, in summary, the present invention is based on the finding that when used in very low doses, i.e. below the levels used in epilepsy or mood disorders, anti-epileptic drugs can improve alone or in combination with stimulants in adults and children suffering from ADHD.

Accordingly, in a first aspect, the present invention provides a method of treating attention deficit hyperactivity disorder (ADHD) in an individual suffering from said disorder but not epilepsy or bipolar disorder, which method comprises administering to the individual an anti-epileptic mood stabiliser at a dose which is sub-therapeutic for mood stabilisation.

The present invention also provides a method of improving cognitive function and/or psychosocial functioning in an individual suffering from attention deficit hyperactivity disorder (ADHD), which method comprises administering to the individual an anti-epileptic mood stabiliser at a dose which is sub-therapeutic for mood stabilisation.

Preferably the patient does not suffer from epilepsy or bipolar disorder.

In a related aspect, the present invention provides a method of treating attention deficit hyperactivity disorder (ADHD) in an individual suffering from said disorder but not epilepsy or bipolar disorder, which method comprises administering to the individual (i) an anti-epileptic mood stabiliser at a dose which is sub-therapeutic for mood stabilisation and (ii) a psychostimulant.

The present invention also provides a method of improving cognitive function and/or psychosocial functioning in an individual suffering from attention deficit hyperactivity disorder (ADHD), which method comprises administering to the individual an anti-epileptic mood stabiliser at a dose which is sub-therapeutic for mood stabilisation, and a psychostimulant.

Preferably the patient does not suffer from epilepsy or bipolar disorder.

In a related aspect, the present invention also provides a method of treating attention deficit hyperactivity disorder (ADHD) comprising:
 a) identifying a subject in need of treatment for ADHD;
 b) administering therapeutically effective amounts of an anti-epileptic mood stabiliser and optionally a psychostimulant so as to improve the subject's cognitive function and/or psychosocial functioning.

The present invention also provides an anti-epileptic mood stabiliser for use in a method of treating ADHD and in improving cognitive function and/or psychosocial functioning as referred to above as well as the use of an anti-epileptic mood stabiliser in the manufacture of a medicament for use in such a method.

The present invention further provides a combination of an anti-epileptic mood stabiliser and a psychostimulant for use in a method of treating ADHD and improving cognitive function and/or psychosocial functioning as referred to above as well as the use of a combination of an anti-epileptic mood stabiliser and a psychostimulant in the manufacture of a medicament for use in such a method.

In a second aspect, the present invention provides a method of improving reading comprehension in an individual suffering from learning difficulties, such as reading difficulties, which method comprises administering to the individual an anti-epileptic mood stabiliser.

In a related aspect, the present invention provides a method of improving reading comprehension and/or fluency in an individual suffering from learning difficulties, such as reading difficulties, which method comprises administering to the individual an anti-epileptic mood stabiliser and a psychostimulant.

In a related aspect, the present invention also provides a method of treating learning difficulties comprising:
 a) identifying a subject in need of treatment for learning difficulties;
 b) administering therapeutically effective amounts of an anti-epileptic mood stabiliser and optionally a psychostimulant such that the subject's reading comprehension and/or fluency is improved.

The present invention also provides an anti-epileptic mood stabiliser for use in a method of improving reading comprehension and/or fluency as referred to above as well as the use of an anti-epileptic mood stabiliser in the manufacture of a medicament for use in such a method.

The present invention further provides a combination of an anti-epileptic mood stabiliser and a psychostimulant for use in a method of improving reading comprehension and/or fluency as referred to above as well as the use of a combination of an anti-epileptic mood stabiliser and a psychostimulant in the manufacture of a medicament for use in such a method.

In a third aspect, the present invention provides a method of treating ocularmotor dysfunction in an individual suffering from learning difficulties which method comprises administering to the individual an anti-epileptic mood stabiliser, and optionally a psychostimulant.

The present invention also provides an anti-epileptic mood stabiliser, optionally in combination with a psychostimulant, for use in a method of treating ocularmotor dysfunction as referred to above as well as the use of an anti-epileptic mood stabiliser, optionally in combination with a psychostimulant, in the manufacture of a medicament for use in such a method.

In a fourth aspect, the present invention provides a method of treating abnormal saccadic eye movements in an individual which method comprises administering to the individual an anti-epileptic mood stabiliser and optionally a psychostimulant.

The present invention also provides an anti-epileptic mood stabiliser, optionally in combination with a psychostimulant, for use in a method of treating abnormal saccadic eye movements as referred to above as well as the use of an anti-epileptic mood stabiliser, optionally in combination with a psychostimulant, in the manufacture of a medicament for use in such a method.

In a fifth aspect, the present invention provides a method of improving cerebellar-mediated motor planning and sequencing in an individual, such as an individual suffering from learning difficulties, which method comprises administering to the individual an anti-epileptic mood stabiliser, and optionally a psychostimulant.

The present invention also provides an anti-epileptic mood stabiliser, optionally in combination with a psychostimulant, for use in a method of improving cerebellar-mediated motor planning and sequencing in an individual, such as an individual suffering from learning difficulties, as referred to above as well as the use of an anti-epileptic mood stabiliser, optionally in combination with a psychostimulant, in the manufacture of a medicament for use in such a method.

In the various aspects mentioned above, it is preferred that the individual does not suffer from epilepsy or bipolar disorder.

In a particularly preferred embodiment of the different aspects mentioned above, the dose of the anti-epileptic mood stabiliser administered to the individual is sub-therapeutic for mood stabilisation.

We have extended outside the area of ADHD the cognitive benefits identified with the use of low dose anti-epileptic mood stabiliser.

The ability to communicate effectively, sequence and organise thoughts is an essential aspect of all human interaction and communication. This is considered to be dependent on higher executive functioning which serve to coordinate and integrate the cognitive functioning of the brain. When this is impaired it can lead to frustration and the perceived inability to have a sense of control in general social functioning. This can be conceptualised as a deficit of higher executive functioning, and is associated with a poorer psychosocial outcome in all psychological conditions. Without the ability to establish and maintain positive interpersonal relationships the individual is more vulnerable to a poorer outcome from negative life events.

Following our success with ADHD patients, we hypothesised that the benefits noted in ADHD from the use of low dose anti-epileptics may also be obtained in other conditions where the individual displayed a deficit in the ability to sequence and organise their thoughts which could lead to an impairment in psychological functioning. This deficit may also lead to the development of anxiety due to the inability to control the focus of attention, thereby resulting in a pathological focus on noxious stimuli.

We have subsequently noted clinically that in other conditions particularly where there are commonly such impairments such as with anxiety, the use of low dose anti-epileptics can also result in sustained improvement in function and a reduction in symptoms. This has been noted specifically in the treatment of Generalised Anxiety Disorder with a dose of 50 to 150 mg of sodium valproate without the co-administration of a stimulant.

Thus the improvements obtained with ADHD patients address cognitive deficiencies that are also seen in other disorders that fall within the DSM-IV-TR classification, in particular: Communication Disorders (e.g. Expressive Language Disorder, Mixed Receptive-Expressive Language Disorder, Phonological Disorder, Stuttering, Communication Disorder NOS (=Not Otherwise Specified); Pervasive Development Disorders (Autistic Spectrum Disorders such as Autistic Disorder and Asperger's Disorder; Rett's Disorder, Childhood Disintegrative Disorder and Pervasive Developmental Disorder NOS); and Anxiety Disorders (e.g. Generalized Anxiety Disorder).

Accordingly, in a sixth aspect, the present invention also provides a method of treating a disorder selected from the group consisting of Communication Disorders; Pervasive Development Disorders; and Anxiety Disorders in an individual suffering from said disorder but not epilepsy or bipolar disorder, which method comprises administering to the individual an anti-epileptic mood stabiliser at a dose which is sub-therapeutic for mood stabilisation.

It is preferred that the individual does not suffer from epilepsy or bipolar disorder. In a seventh aspect, the present invention provides a pharmaceutical kit comprising a first pharmaceutical composition comprising (i) an anti-epileptic mood stabiliser together with a pharmaceutically acceptable carrier or diluent and (ii) a second pharmaceutical composition comprising a psychostimulant together with a pharmaceutically acceptable carrier or diluent. Preferably the first pharmaceutical composition is provided as a dosage unit containing a dose of anti-epileptic mood stabiliser which is sub-therapeutic for mood stabilisation. The kit may also include instructions for use of the combination of the first and second pharmaceutical compositions in one or more of the methods of the first and second aspects of the invention. The pharmaceutical compositions are preferably formulated for oral administration (e.g. tablets, capsules, syrups, elixirs and the like) or as a patch.

In a related aspect, the present invention provides a pharmaceutical composition comprising an anti-epileptic mood stabiliser and a psychostimulant together with a pharmaceutically acceptable carrier or diluent. Preferably the pharmaceutical composition is provided as a dosage unit containing a daily, or sub-daily, dose of anti-epileptic mood stabiliser which is sub-therapeutic for mood stabilisation together with a daily, or sub-daily dose of the psychostimulant. The pharmaceutical composition is preferably formulated for oral administration (e.g. tablets, capsules, syrups, elixirs and the like). In one embodiment, the mood stabiliser is selected from sodium valproate, or a derivative thereof, topiramate, carbamazepine, pregabalin or phenytoin and the daily dose of the mood stabiliser is as specified below in the detailed description for these compounds. In a related embodiment, the pyschostimulant is selected from methylphenidate, amphetamines (e.g. dextroamphetamine or mixed amphetamine salts) and pemoline and the daily dose of the pyschostimulant is as specified below in the detailed description for these compounds.

DETAILED DESCRIPTION OF THE INVENTION

Unless defined otherwise, all technical and scientific terms used herein have the same meaning as commonly understood by one of ordinary skill in the art (e.g. in pharmaceutical chemistry and medicine, including psychiatry).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to numerical values, unless stated otherwise, is to be taken as meaning "about" that numerical value. The term "about" is used to indicate that a value includes the inherent variation of error for the device and the method being employed to determine the value, or the variation that exists among the study subjects.

In one aspect, the present invention relates to methods of treating individuals with attention-deficit hyperactivity disorder (ADHD). ADHD is a developmental disorder distinguished by symptoms of inattention, hyperactivity and impulsivity. Although ADHD is one of the most frequently diagnosed psychological disorders in childhood, long-term studies have demonstrated that symptoms are often maintained into adulthood. Diagnostic criteria for ADHD are given in the Fourth Edition of the Diagnostic and Statistical Manual of Mental Disorders (American Psychiatric Association, 2000), referred to as DSM-IV-TR. See also Snyder, Nussbaum, & Robins (Eds.), 2006, ibid (especially Box 2) and Weiss & Murray, 2003, ibid.

Individuals with ADHD may also have other disorders such as epilepsy or bipolar disorder. In embodiment it is preferred that the individual who it is desired to treat does not suffer from epilepsy or bipolar disorder (the latter typically as defined in DSM-IV-TR). It may also be preferred that the individual does not suffer from a psychotic disorder.

The treatment of such individuals using the methods of invention is typically intended to improve cognitive function and/or psychosocial functioning in the individuals. The term "cognitive function and/or psychosocial functioning" includes executive function, informational processing, verbal comprehension, verbal expression/fluency, reading comprehension/fluency, saccadic eye movements, non-verbal feedback/behaviour in response to verbal interaction, interpersonal interaction and the like.

In a second aspect, the present invention relates to methods of treating individuals with learning difficulties, such as reading difficulties/disorders and language disorders, which can include ADHD sufferers but also includes non-ADHD sufferers.

In a related aspect, the present invention relates to methods of treating individuals with ocularmotor dysfunction in individuals suffering from learning difficulties, such as reading difficulties/disorders and language disorders, which again can include ADHD sufferers but also includes non-ADHD sufferers. Ocularmotor dysfunction includes faulty/abnormal saccades, such as deficiencies in suppressing fast saccades. Saccades are the rapid eye movements that take the eyes from one word to the next. When we read, we make mostly forward saccades. Backward saccade movements are used to read something over again for better comprehension. Individuals with reading difficulties, including reading comprehension, often have more frequent backward saccades than normal individuals.

We have found the use of low doses of anti-epileptic mood stabilisers can improve eye movements (as assessed using the Developmental Eye Movement test) compared with and without treatment with stimulant alone. At higher doses of the anti-epileptic this benefit is lost and can cause a slowing in the measurements relative to base line. With thus hypothesise that in some patients the low dose anti-epileptic is improving the visual-verbal automaticity and thus improving the reading ability. We suggest that this is through an improvement in the faulty saccades.

Thus, in another aspect, the present invention relates to methods of treating abnormal saccadic eye movements in individuals, such as individuals with learning difficulties, such as reading difficulties/disorders and language disorders, which again can include ADHD sufferers but also includes non-ADHD sufferers. Such individuals may have difficulties in fixation and suppressing fast saccades, especially backwards saccades. Thus the term "abnormal saccadic eye movements" includes more frequent backward saccades. The term also includes increased saccadic latency. The methods of the invention may also be directed to improving antisaccades performance in an individual, e.g. accuracy and/or response times.

The results that we have obtained also indicate that anti-epileptic mood stabilisers are having a beneficial effect on cerebellar function, especially in relation to motor planning and sequencing which is often impaired in patients with learning difficulties. The cerebellum is believed to be involved in timing of movement and the automation of skills. Whilst impairment of these functions may be particularly noticeable in patients with learning difficulties, individuals who would not be considered to have learning difficulties in the conventional sense may also benefit from the treatments described herein to improve skill acquisition and coordination, particularly left and right hemisphere coordination. Accordingly, the invention also provides methods for improve skill acquisition and coordination, such as left and right hemisphere coordination, by administering to individuals anti-epileptic mood stabilisers and optionally psychostimulants as described herein in the various other aspects. Such individuals include, but are not limited to, those with learning difficulties.

Individuals with learning difficulties include dyslexic individuals and those with non-verbal learning disorders, such as phonological deficiencies. Learning difficulties include reading, writing and spelling difficulties.

Further the improvements obtained with ADHD patients address cognitive deficiencies that are also seen in other disorders that fall within the DSM-IV-TR classification, in particular: Communication Disorders (e.g. Expressive Language Disorder, Mixed Receptive-Expressive Language Disorder, Phonological Disorder, Stuttering, Communication Disorder NOS (=Not Otherwise Specified); Pervasive Development Disorders (Autistic Spectrum Disorders such as Autistic Disorder and Asperger's Disorder; Rett's Disorder, Childhood Disintegrative Disorder and Pervasive Developmental Disorder NOS); and Anxiety Disorders (e.g. Generalized Anxiety Disorder).

Accordingly, the present invention also provides a method of treating a disorder selected from the group consisting of Communication Disorders; Pervasive Development Disorders; and Anxiety Disorders in an individual suffering from said disorder but not epilepsy or bipolar disorder, which method comprises administering to the individual an anti-epileptic mood stabiliser at a dose which is sub-therapeutic for mood stabilisation. In particular, the methods of the invention may be used to improve cognitive function and/or psychosocial functioning an individual suffering from one or more of these disorders.

The methods of the invention may be used to treat children or adults. For examples, patients may be pre-pubescent, at least 16 years old or at least 18 years old.

The methods of the invention involve administering to the individual an anti-epileptic mood stabiliser, also referred to as an anticonvulsant. Combinations of two or more mood stabilisers may also be administered.

A large number of anti-epileptic mood stabilisers (anticonvulsants) are known in the art and include barbiturates (e.g. primidone, Phenobarbital, Barbexaclone), benzodiazepines (e.g. diazepam, clorazepate, clonazepam, clobazam), carboxamides (e.g. carbamazepine ((Z)-5H-dibenzo[b,f] azepine-5-carboxamide), oxcarbazepine (10,11-Dihydro-10-oxo-5H-dibenz[b,f]azepine-5-carboxamide), valpromide), fatty acids (e.g. tiagabine ((3S)-1-[4,4-bis(3-methylthiophen-2-yl)but-3-enyl]piperidine-3-carboxylic acid) and the valproates—valproic acid, sodium valproate and divaiproex sodium), hydantoins (e.g. ethotoin (3-ethyl-5-phenyl-imidazolidine-2,4-dione), phenytoin (5,5-diphenylimidazolidine-2,4-dione), fosphenytoin sodium, mephenytoin), oxazolidinediones (e.g. trimethadione, paramethadione, ethadione), succinimides (e.g. ethosuximide, phensuximide), pyrrolidines (e.g. levetiracetam), sulfonamides (e.g. acetazolamide, methazolamide, zonisamide, sultiame), aminobutyric acids, sulfamate-substituted monosaccharides (e.g. topiramate (2,3:4,5-Bis-O-(1-methylethylidene)-beta-D-fructopyranose sulfamate)), gaba analogs (e.g. gabapentin (2-[1-aminomethyl)cyclohexyl]acetic acid), pregabalin ((S)-3-(aminomethyl)-5-methylhexanoic acid)), trizines (e.g. lamotrigine), felbamate, losigamone, pheneturide, rufinamide, vigabatrin and so on. Particular examples include sodium valproate (sodium di-n-propylacetic acid) and derivatives thereof (valproic acid, valproate pivoxil, semi-sodium valproate, divalproex, valproylamides such as valpromide, Depakene, Depakote, Depakote ER), tiagabine, ethosuximide, zonisamide, carbamazepine, oxcarbazepine, lamotrigine, tiagabine, gabapentin, pregabalin, phenytoin, primidone, phenobarbitone, phenobarital, topiramate, diazepam and related compounds, and levetiracetam. Particularly preferred are sodium valproate and derivatives thereof, tiagabine, topiramate, carbamazepine, oxcarbazepine, ethotoin, phenytoin, gabapentin and/or pregabalin. It will be appreciated by a person skilled in the art that reference to the various compounds referred to above includes pharmaceutically acceptable salts thereof, as appropriate. In addition, many of the compounds referred to above are available in different formulations, such as slow release, extended release. All such formulations are encompassed within the scope of the present invention for use in the methods of the invention.

In one embodiment, the mood stabiliser is a gamma-aminobutyric acid (GABA) enhancer, i.e. a GABAergic agent.

The dose administered of the mood stabiliser is sub-therapeutic with respect to mood stabilisation, controlling seizures and/or mania. This means that the dose administered is below the dose range that would be administered to epileptics and individuals with bipolar disorders to achieve mood stabilisation, control of seizures and/or control of mania, as appropriate. As mentioned above, the use of such sub-therapeutic dosages is advantageous for the treatments described herein. For comparison, in the case of sodium valproate, the product information for Epilim (Sanofi-Aventis) states that, for the treatment of mania (e.g. bipolar disorder) in adults, control of symptoms typically occurs within the range of 1,000 to 2,000 mg/day, (i.e. approximately 20 to 30 mg/kg/day). In the case of carbamazepine, a typical dose for treating epileptic seizures is in the range of from 400 to 800 mg/day. In the case of topiramate, the target dose for controlling epileptic seizures is between 100 to 500 mg/day.

By contrast, in relation to sodium valproate (and derivatives thereof), a sub-therapeutic dose with respect to mood stabilisation is considered in this context to be less than 400 mg/day or 4 mg/kg/day, a preferred dose being less than 300 mg/day. The minimum dose is typically at least 25 mg/day, such as at least 50 or 100 mg/day, or at least 0.3, 0.5 or 1 mg/kg/day. The doses are expressed both independently of patient weight and based on patient weight since minimum and maximum doses can apply. Typically, the mg/kg/day is more commonly applied in relation to children whereas the total mg/day may be more appropriate for adults. These dosages in relation to sodium valproate and derivatives thereof represent, at the upper end, less than 50% of the lower end of the normal therapeutic dose range for treating epilepsy/bipolar disorder, and at the lower end, about 5 to 10% of the normal therapeutic dose range for treating epilepsy/bipolar disorder. These dosages can be used as a guide for calculating the relative dosages of other mood stabilisers that would constitute a sub-therapeutic dose.

For example, in the case of carbamazepine, a preferred sub-therapeutic dose is in the range of from 25 to 200 mg/day, such as more than 50, 75 or 100 mg/day but less than 250 200 or 150 mg/day. In the case of topiramate, a preferred sub-therapeutic dose is in the range of from 6.25 to 75 mg/day, such as at least 10, 15, 20, 30 or 40 mg/day but less than 80, 75 or 60 mg/day. In the case of phenytoin, a preferred sub-therapeutic dose is in the range of from 20 to 80 mg/day, such as more than 30 or 40 mg/day but less than 70 or 60 mg/day. In the case of pregabalin, a preferred sub-therapeutic dose is in the range of from 30 to 80 mg/day, such as more than 30 or 40 mg/day but less than 80 or 70 mg/day.

Preferably, the sub-therapeutic dose is less than 50%, such as less than 40% or 30%, of the minimum dose that would be administered to epileptics and individuals with bipolar disorders to achieve mood stabilisation, control of seizures and/or control of mania, as appropriate. For example we have found that 10% of the normal minimum dose that would be administered to epileptics and individuals with bipolar disorders to achieve mood stabilisation, control of seizures and/or control of mania, as appropriate, works well for the particular compounds tested in human subject. Typically the sub-therapeutic dose is at least 2.5, 5 or 10% of the minimum dose that would be administered to epileptics and individuals with bipolar disorders to achieve mood stabilisation, control of seizures and/or control of mania, as appropriate.

The following is a list of AED with their usual minimum anti-convulsant dose to enable a calculation of an estimate of the initial low dose AED dose. A sub-therapeutic dose for mood stabilisation in the context of the present invention is therefore preferably less than 50%, such as less than 40% or 30% of the minimum dosages listed below for each particular drug e.g. for Ethotin, a sub-therapeutic dose is less than 500 mg/day, such as less than 400 or 300 mg/day. The minimum dose to be administered in the context of the present invention is preferably at least 2.5, 5 or 10% of the minimum therapeutic dose for mood stabilisation listed below, e.g. in the case of Ethotoin, at least 25, 50 or 100 mg/day.

| Drug | Minimum Dose/day effective for mood stabilisation |
|---|---|
| Barbexaclone | 200 mg in divided doses |
| Carbamazepine | 400 mg |
| Clobazam | 5 mg/kg daily |
| Clonazepam | 1 mg |
| Ethadione | 1000 mg |
| Ethosuximide | 1000 mg |
| Ethotoin | 1000 mg |
| Felbamate | 1200 mg |
| Fosphenytoin Sodium | 10 mg/kg |
| Gabapentin | 900 mg |
| Lamotrigine | 100 mg |
| Levetiracetam | 1000 mg |
| Losigamone | 1500 mg |
| Mephenytoin | 200 mg |
| Oxcarbazepine | 600 mg |
| Pheneturide | 600 mg |
| Phenytoin | 200 mg |
| Pregabalin | 300 mg |
| Primidone | 750 mg |
| Rufinamide | 400 mg |
| Sultiame | 200 mg |
| Tiagabine Hydrochloride | 30 mg |
| Topiramate | 100 mg |
| Vigabatrin | 1000 mg |
| Zonisamide | 200 mg |

It is preferred that the dosage administered of mood stabiliser/anti-convulsant is sub-therapeutic for mood stabilisation for the entire, or at least substantially the entire, treatment period. In other words, it is preferred that the dosage administered of mood stabiliser does not exceed the maximum stated sub-therapeutic dosages described above throughout the treatment.

In certain embodiments, the patients receive a combination therapy of a mood stabiliser, at a dose which is sub-therapeutic for mood stabilisation, and a psychostimulant (also termed a CNS stimulant).

A large number of pyschostimulants are known in the art. Examples of psychostimulants which are already approved for use in treating ADHD include methylphenidate, typically as the hydrochloride (e.g. Ritalin™, Ritaline LA™, Focalin™, Concerta™, Methylin, Attenta™, Lorentin™, Daytrana™, Tranquilyn™, Equasym™, Riphenidate™, Rubifen™, Metadate CD™), amphetamines (e.g. dextroamphetamine sulphate (Dexamin™, Dextrostat™, Dexadrine™)/dexamphetamine or mixed amphetamine salts (Adderall XR™)) and pemoline (Cylert™)). Typical doses for these medications are described in Wilens and Dodson, 2004, Clin. Psychiatry 65: 1301-1313 (methylphenidate—juveniles: 0.6 to 1.0 mg/kg/day; adults 20 to 100 mg per day, amphetamine—juveniles: 0.3 to 1.5 mg/kg/day; adults 10 to 70 mg/day, pemoline—juveniles: 1.0 to 3.0 mg/kg/day; adults 75 to 150 mg/day). Combinations of two or more pyschostimulants may be used. References to all pyschostimulant described herein include pharmaceutically acceptable salts thereof, as appropriate, and slow release and extended release formulations.

Other examples include: Eugeroics such as Adrafinil, Armodafinil, Carphedon, Modafinil; Phenethylamines such as 4-Fluoroamphetamine, 4-Fluoromethamphetamine, 4-Methylmethcathinone, 4-MTA, α-PPP, Amphechloral, Amphetamine (Dextroamphetamine, Adderall), Amphetaminil, Benzphetamine, Bupropion, Cathinone, Chlorphentermine, Clobenzorex, Clortermine, Cypenamine, Diethylpropion, Dimethoxyamphetamine, Dimethylamphetamine, Dimethylcathinone, Diphenyl prolinol, Ephedrine, Epinephrine, Ethcathinone, Ethylamphetamine, Fencamfamine, Fenethylline, Fenfluramine, Fenproporex, Feprosidnine, Furfenorex, Levomethamphetamine, Lisdexamfetamine (Vyvance™) (L-lysine-d-amphetamine), MDMA, Mefenorex, Methamphetamine, Methcathinone, Methoxyphedrine, Methylone, Octopamine, Parahydroxyamphetamine, PMA, PMEA, PMMA, PPAP, Phendimetrazine, Phenmetrazine, Phentermine, Phenylephrine, Phenylpropanolamine, Prolintane, Propylamphetamine, Pseudoephedrine, Selegiline, Synephrine, Tenamphetamine, Xylopropamine; Piperazines such as BZP, MeOPP, MBZP, mCPP, 2C-B-BZP; Xanthines such as Caffeine, Aminophylline, Paraxanthine, Theobromine, Theophylline; Tropanes such as Brasofensine, CFT, Cocaethylene, Cocaine, Dimethocaine, Lometopane, PIT, PTT, RTI-121, Tesofensine, Troparil, WF-23, WF-33; Cholinergics such as Arecoline, Cotinine, Nicotine; Convulsants such as Bicuculline, Gabazine, Pentetrazol, Picrotoxin, Strychnine, Thujone; Phenylaminooxazoles such as 4-Methyl-aminorex, Aminorex, Clominorex, Fenozolone, Fluminorex, Pemoline, Thozalinone; Others such as Amineptine, Bemegride, BPAP, Clenbuterol, Clofenciclan, Cyclopentamine, Cyprodenate, Desoxypipradrol, Ethylphenidate, Ethamivan, Gilutensin, GYKI-52895, Hexacyclonate, Indanorex, Indatraline, Isometheptene, Mazindol, MDPV, Mesocarb, methylphenidate, Dexmethylphenidate, Naphthylisopropylamine, Nikethamide, Nocaine, Nomifensine, Phacetoperane, Phthalimidopropiophenone, Pipradrol, Prolintane, Propylhexedrine, Pyrovalerone, Tuamine, Vanoxerine, Yohimbine, Zylofuramine, Deanol, Diethylaminoethanol, Dimefline Hydrochloride, Etilamfetamine Hydrochloride, Fencamfamin Hydrochloride, Fenetylline Hydrochloride, Fenfluramine Hydrochloride, Fenproporex Hydrochloride, Lobeline Hydrochloride, Pentetrazol, Propylhexedrine.

Particularly preferred combinations of mood stabilisers and psychostimulants are: (i) one or more of sodium valproate and derivatives thereof, topiramate, carbamazepine, oxcarbazepine, phenytoin, gabapentin and/or pregabalin together with (ii) one or more of methylphenidate (Ritalin™, Ritaline LA™, Focalin™, Concerta™, Metadate CD™), amphetamines (e.g. dextroamphetamine (Dexadrine™), Lisdexamfetamine (Vyvance™) (L-lysine-d-amphetamine) or mixed amphetamine salts (Adderall XR™)) and pemoline (Cylert™)). For example: sodium valproate (or a derivative thereof) and methylphenidate; sodium valproate (or a derivative thereof) and dextroamphetamine sulphate; topiramate and methylphenidate; topiramate and dextroamphetamine sulphate; phenytoin and methylphenidate; phenytoin and dextroamphetamine sulphate.

In certain alternative embodiments, the patients receive a combination therapy of a mood stabiliser, at a dose which is sub-therapeutic for mood stabilisation, and a non-stimulant treatment for ADHD. In a preferred embodiment, the non-stimulant is a noradrenaline (norepinephrine) and/or dopamine reuptake inhibitor, preferably Atomoxetine (3R)—N-methyl-3-(2-methylphenoxy)-3-phenyl-propan-1-amine), typically administered as the hydrochloride, Buprorion ((±)-2-(tert-butylamino)-1-(3-chlorophenyl)propan-1-one), Venlafaxin (1-[2-dimethylamino-1-(4-methoxyphenyl)-ethyl] cyclohexan-1-ol), or Devenlafaxin. Other examples include sibutramine, nefazodone, milnacipran, desipramine, duloxetine and bicifadine. For the avoidance of doubt, the non-stimulants can be applied to all embodiments that refer to combination therapy with anti-epileptic drugs and psychostimulants, the non-stimulants being administered or present in place of, or in addition to, said psychostimulants.

The mood stabiliser and psychostimulant/non-stimulant may be administered separately, sequentially or concomitantly, as appropriate.

Typically, the mood stabiliser and, where required, the psychostimulant/non-stimulant are formulated with a pharmaceutically acceptable carrier or diluent to form separate or combined pharmaceutical compositions. Suitable pharmaceutical carriers are described in "Remington's Pharmaceutical Sciences" by E. W. Martin. Mack Publishing Co., Easton, Pa., 1990.

Pharmaceutical dosage forms include oral dosage forms such as tablets, capsules, syrups, elixirs; patches; sterile solutions, powders for inhalation/nasal delivery; suspensions for injectable administration, and other compositions known in the art. Compounds may be formulation for slow release, extended release etc.

Suitable routes of administration will vary depending on the active compounds used and dosage form, and include topical, enteral and parenteral (such as oral intranasal, intravenous, intramuscular, subcutaneous, transdermal).

The optimal dose, route (e.g. oral) and frequency of administration (e.g. once, twice, three times or four times daily) of the mood stabiliser and psychostimulant can be determined by a person skilled in the art based on, for example, the patient age, severity of symptoms, weight, diet and time of administration, and taking into account the guidance as to dose provided above. In the case where the mood stabiliser is sodium valproate, the dose is typically from 25 mg/day to 400 mg/day (from 0.3 mg/kg/day to 4 mg/kg/day), preferably less than 300 or 200 mg/day or less than 4, 3 or 2 mg/kg/day. The minimum dose of sodium valproate (particularly for adults) is typically at least 25 or 50 mg/day, such as at least 100 mg/day, or at least 0.3, 0.5 or 1 mg/kg/day. These dosage ranges can be used as guidance by a person skilled in the art when determining dosage ranges for other mood stabilisers. For example, see above in relation to carbamazepine, pregabalin, phenytoin and topiramate.

Typical dosage ranges for psychostimulants are from 5 to 150 mg/day, such as from 10 to 120 mg/day. Specific guidance in relation to particular psychostimulants is given above.

The period of treatment will generally vary from patient to patient but is typically of at least 6 months, duration, such at least 12 months. In the 18 months since or first trials of the combination of a low dose anti-epileptic and stimulant were begin, there has been in the vast majority of subjects a sustained and significant benefit following the addition of a low dose anti-epileptic to their therapy. There is no apparent loss of efficacy from the low dose AED. Indeed, often the contrary is noted with a reduction in the dose without loss of clinical benefit. Accordingly, the methods of the invention may involve a reduction in the dose of anti-epileptic drug as the treatment progresses, e.g. a reduction of from 10 to 20, 30 or 40% after 2 to 6 months.

The dose of mood stabiliser, and psychostimulant where appropriate, administered is selected so as to provide a therapeutically effective amount to achieve the intended purpose. In the context of the present invention, the intended purpose in the first aspect is to treat ADHD, such as to improve the patient's cognitive function and/or psychosocial functioning and/or to alleviate ADHD behavioural symptoms. Particular functions include executive function, informational processing, verbal comprehension, reading comprehension, saccadic eye movements, non-verbal feedback/behaviour in response to verbal interaction, interpersonal interaction and the like.

Assessment of cognitive function and/or psychosocial functioning and or ADHD behavioural symptoms to determine whether such an improvement has occurred can be conducted as described in the examples. Assessments include measurement of: information processing speed, concentration effectiveness, switching of attention between tasks, ability to maintain attention and inhibit impulsive responses, working memory capacity (e.g. using WebOSPAN), response inhibition, visual scanning, reading comprehension (e.g. using all or part of the Nelson-Denny Reading Test: Brown, Fishco, & Hanna, 1993, Itasca, Ill.: Riverside Publishing), the clinical assessment of oculomotor function, saccadic eye movements (e.g. using Developmental Eye Movements Test (DEM) version 1, Richman & Garzia, 1987; ReadAlyzer™ Eye Movement Recording system. Compevo AB and/or the scleral search coil technique: Irving et al., 2003, Invest Ophthalmol Vis Sci. 44(5): 1933-8 and references therein), pseudo-word decoding (e.g. using Wechsler Individual Achievement Test-II). Many of the above tests can be conducted using WebNeuro (Brain Resource Company—brainresource.com).

The intended purpose in the second aspect is to improve reading comprehension in a patient suffering from learning difficulties. Improvements in reading comprehension can be assessed using, for example, all or part of the Nelson-Denny Reading Test.

The intended purpose in the third aspect to treat or reduce ocularmotor dysfunction in an individual suffering from learning difficulties. Improvements in ocularmotor function can be assessed using, for example, using Developmental Eye Movements Test (DEM) version 1, Richman & Garzia, 1987; ReadAlyzer™ Eye Movement Recording System. Compevo AB, and/or the scleral search coil technique (Irving et al., 2003, Invest Ophthalmol Vis Sci. 44(5): 1933-8 and references therein).

The intended purpose in the fourth aspect is to treat or reduce abnormal saccadic eye movements in an individual, such as an individual suffering from learning difficulties. Saccadic eye movements can be assessed using, for example, using Developmental Eye Movements Test (DEM) version 1, Richman & Garzia, 1987; ReadAlyzer™ Eye Movement Recording system. Compevo AB. and/or the scleral search coil technique (Irving et al., 2003, Invest Ophthalmol Vis Sci. 44(5): 1933-8 and references therein)

The intended purpose in the fifth aspect is to improve cerebellar-mediated function, especially in relation to motor planning and sequencing, which is often impaired in patients with learning difficulties.

The intended purpose in the sixth aspect is to treat a disorder selected from the group of DSM-IV-TR diagnostic categories consisting of Communication Disorders; Pervasive Development Disorders; and Anxiety Disorders.

A further intended purpose is to improve skill acquisition and coordination, such as left and right hemisphere coordination, individuals which include, but are not limited to, those with learning difficulties.

The present invention will now be further described with reference to the following examples, which are illustrative only and non-limiting.

Example 1

Treatment of Adult ADHD Sufferers with a Combination of Psychostimulant and Mood Stabiliser In the clinical setting where this study has originated from, a number of adults with ADHD (who had previously demonstrated significant improvements on stimulants alone) began a dual regime of stimulant medication (dexamphetamine) augmented with sodium valproate (VPA), primarily as an agent to improve mood stability.

The initial dosages used were from 15 to 70 mg/day of dexamphetamine and from 100 to 700 mg/day of VPA (Epilim) (=approximately 2 to 10 mg/kg/day). The Epilim product information supplied by Sanofi-Aventis for the treatment of mania (e.g. bipolar disorder) in adults suggests that control of symptoms occurs within the range of 1,000 to 2,000 mg/day, (i.e. 20 to 30 mg/kg/day). The dosages used in this trial were therefore substantially lower than the dosages required for treating mania.

The determination of the dose for the dexamphetamine was undertaken in a clinical sensitive open label manner. The dose was titrated upwards dependent on the clinical response and the freedom from side-effects. The dose range was between 15 and 70 mg a day. The frequency of the dosing also varied dependent upon the clinical response. The usual dose interval was between two to four hours. This dosing adjustment took place prior to the commencement of the sodium valproate. The sodium valproate medication was initiated once a day at 50 mg tablet or elixir and titrated upwards dependent on response, but not more than one increase every three days. The dose was given as a once or twice a day regime. During the titration phase, if clinically possible, no other adjustments to the pharmacotherapy were undertaken.

Following the initial results, the dosages for those patients on the higher dosages of sodium valproate (i.e. 500 or 700 mg) were re-titrated because such patients frequently experienced general cognitive and a resultant loss of efficacy. The dosages of sodium valproate, after adjustment, varied between 50 mg/day, 100 mg/day, 150 mg/day or 200 mg/day (number of patients—120), with the majority of patients receiving between 50 to 150 mg/day with 300 mg/day usually the maximum.

Results and Discussion

When VPA was integrated into the pharmacological approach, patients often described their thoughts as slowing to a rate that was more manageable and less chaotic. This seemed to allow for more temporal sequencing of ideas, with a resulting overall improvement in psychosocial functioning. The interesting dimension to this argument of pharmacological approach is that a large number of these patients had no evidence to suggest a personal or family history of a bipolar disorder and were benefiting from a dose of VPA below the initiation dose recommended for bipolar disorder, and significantly below the dose typically required to achieve control of symptoms of mania.

The results were assessed using the Conners Adult ADHD Rating scales completed by the patient and observer (usually partner or parent). In a sample of 26 patients who completed self CAARS rating scales at; pre treatment, stable on stimulant and stable on anti-epileptic drug (AED). 6 Of the 8 CAARS subscales showed significant quadratic improvement of at least $p<0.5$ after the addition of their AED to their stimulant therapy. With CAARS ADHD symptoms subscale the quadratic significance reached $p<0,001$. Robust improvement was similarly noted on the Quality of Life Scales. A visual analogue scale which was used to compare the subjective benefit of addition of their AED to their initial experience of commencing stimulants showed that the two interventions were of similar benefit. This is significant in the context of the well reported robust treatment effect achieved on initiation of stimulants. The clinical reviews were consistent with the above findings.

A significant number of patients who reported a subjective improvement in ADHD symptoms also described an improvement in their reading and verbal comprehension abilities. They were more able to attend to the content of both the text and conversation, which was in direct contrast to their previously frustrating experiences of needing to put most of their mental effort into either reading or listening with relatively little comprehension occurring. We have been able to assess objectively oculomotor function with the Developmental Eye Movement Test (DEM): this has shown improvement consistent with that of the patient's own subjective experience, with less mental effort required to follow or track written text. This leads us to the hypothesis that the low dose of the sodium valproate is having a beneficial effect on fixational and saccade activity during reading and non reading tasks. The magnitude of the change for many of these individuals was comparable to changes in behaviour that occurred during their first experience of stimulant therapy.

Additionally, the self-reported improvement appeared to correlate closely to notable changes in the complex interpersonal interaction during the clinical consultation. Verbal interactions between the treating psychiatrist and patients appeared more spontaneous and fluid, and patients appeared to be able to provide a higher level of subtle non-verbal feedback during conversations. It would appear, based on this appropriate non-verbal behaviour, that patients were experiencing a greater understanding of the content of the conversation. Patients also reported that reading seemed to require less effort, resulting in greater enjoyment in a task that had previously been very cognitively demanding. This clinical observation would appear to be consistent with the hypothesis by Samuelsson et al. (2004) that ADHD symptoms were more associated with impaired reading comprehension than with word decoding. The improvement as described by patients occurred almost immediately on initiation of therapy, prior to the opportunity for any additional learning to take place. Further, this would seem to preclude the acquisition of further decoding ability as a possible explanation for this improvement.

During the initial trials higher doses in excess of 400 mg were routinely used for some patients (VPA being relatively well tolerated). However doses above this level frequently led to general cognitive slowing and the resultant loss of efficacy. The patients often ceased the medication as a consequence of this and it was only on later re challenge with a lower dose with a much slower re-titration that the ideal and more efficacious dose was identified.

From these observations it has been hypothesised that VPA has a synergistic effect with stimulant medication at a dose that would be considered sub-therapeutic if used only for mood stabilisation. This novel use of VPA has the potential to further enhance our understanding and improve the treatment outcome of those diagnosed and treated with stimulants for ADHD.

Example 2

Clinical Study Protocol

In this study, the combination of an anti-epileptic mood stabiliser in conjunction with stimulant medication as described in Example 1 is investigated in more detail in a clinical study.

The study is based on a combined regime of stimulant (dexamphetamine) and anti-epileptic mood stabiliser (sodium valproate) treatment for adults with ADHD. The effectiveness of the combined regime is assessed in the following domains of functioning:
a) ADHD behavioural symptoms;
b) Executive functioning;
c) Information processing;
d) Reading comprehension; and
e) Quality of life.

| | |
|---|---|
| Title of Trial | A Randomised, Double-Blind, Placebo-Controlled, Parallel-Arm, Phase II, Dose-Ranging Study of the Efficacy and Safety of Sodium Valproate in Adults with Attention Deficit Disorder on a Stable Dose of Dexamphetamine |
| Trial Centre | Single-Centre Study based in Queensland, Australia |
| Planned Trial Duration | 8 weeks |
| Trial Phase | II |
| Objectives | Primary objectives: To assess the efficacy of sodium valproate in treating the symptoms of ADHD in patients stabilised on an optimal dose of dexamphetamine Secondary objectives: To assess the effect of sodium valproate on working memory in ADHD patients stabilised on an optimal dose of dexamphetamine To assess the safety profile of sodium valproate in ADHD patients treated stabilised on an optimal dose of dexamphetamine To assess the effect of sodium valproate on quality of life in ADHD patients treated stabilised on an optimal dose of dexamphetamine Exploratory endpoints: To assess whether there is an optimal dose of required correlates to weight, sex, age or dose of stimulant on which patients remained stabilised |
| Methodology | Single-Centre, Double-Blind, Placebo-Controlled, Parallel, Four-Arm, Dose-Ranging |
| Sample Size | A total of 100 evaluable patients: 25 patients on sodium valproate 50 mg od (once daily) 25 patients on sodium valproate 100 mg od 25 patients on sodium valproate 150 mg od 25 patients on placebo od |
| Patient Selection Criteria | Key Inclusion Criteria Patients of either sex aged 18 to 60 years Women must not be pregnant or breast-feeding Meet DSM-IV criteria for attention deficit hyperactivity disorder Patients describing a chronic course of ADHD symptoms from childhood to adulthood Patients who having been stabilised on a maximum tolerated daily dose of dexamphetamine no lower than 5 mg and no greater than 60 mg for a minimum of 6 weeks Patients who after 6 weeks of treatment with a maximum tolerated dose score at least 30 out of 54 on the investigator rated ADHD-IV scale Written informed consent. Key Exclusion Criteria Patients exposed to anticonvulsants on benzodiazepines within the last 2 months Patients who have taken part in an investigational drug trial within the past 3 months Women who are pregnant or breast-feeding Patients suffering from a mood disorder Patients suffering from a personality disorder Patients with a history of epilepsy Patients who abuse alcohol or drugs Patients for whom dexamphetamine or valproate are contraindicated (allergy to either drug, active liver disease, family history of severe hepatic dysfunction, porphyria, cardiovascular disease, moderate to severe hypertension, hyperexcitability |

-continued

| | |
|---|---|
| | or agitated states, hyperthyroidism, glaucoma, pregnancy, history of alcohol or drug abuse) |
| Schedule of Treatment and Visits | Screening: Patient informed Consent Inclusion/exclusion criteria Semi-structured psychiatric interview ADHD-IV (Investigator Rated) Young Mania Rating Scale Brown's rating scale Paced Auditory Serial Addition Test (PASAT) DEM Adult ADHD Impact Module (AIM-A) Temperature, blood pressure, pulse Weight U&Es, LFTs, TFT ECG Spontaneously reported adverse events During Treatment: Baseline, Weeks 2, 4, 6 and 8 ADHD-IV (Investigator Rated) Brown's rating scale Paced Auditory Serial Addition Test (PASAT) Readalyzer ™ Eye Movement Recording System DEM Adult ADHD Impact Module (AIM-A) Temperature, blood pressure, pulse Weight U&Es, LFTs, TFT Spontaneously On withdrawal: Reason for withdrawal |
| Dosing of Study Drug | 50 mg od, 100 mg od, 150 mg od |
| Concomitant Therapy | Dexamphetamine |
| Trial Medication | Sodium valproate liquid 200 mg per 5 ml Placebo |

Example 3

Clinical Study with Anti-Epileptic Mood Stabilisers Alone

In this trial we studied a group of patients who had symptoms of ADHD (without any associated bipolar disorder) but have been unable to or not wished to or had not yet been able, commence on stimulants, individuals were treated with either sodium vaiproate alone, in the same dose range as prescribed in the combined treatment, or with topiramate (Topamax) alone at a dose of 12.5-50 mg/day, or with Phenytoin alone at a dose of 30-60 mg/day. The improvements assessed using self and other rating scales objective psychometric tool together with repeated clinical assessments. The patients reported improvements in the organisation of thoughts in conversation and reading comprehension. It was also noted in two cases there was both a significant improvement of verbal fluency and abatement of socially impairing co-morbid verbal stutter on initiation of therapy. Additionally the successful completion of tasks improved, changes which were particularly evident and noted by the partners of the patients.

The topiramate was also noted to have an effect on coordination, as well as improved organisation and motivation. This latter observation could be understood as an improvement in the functional output thereby setting up a positive feedback circuit for the individual and sustaining their engagement and thus proficiency in the task.

These observations are very interesting in the context of the possible cerebellar model of coordination of motor activity, which includes that of language.

1. The sequencing of oral language improves, allowing more fluid conversation and temporal organisation of the content. This can be seen by the individuals not having to make such an effort during the interaction, with a greater focus on the content rather than the structure of what they are saying.
2. The sequencing of motor tasks improves with the subjective experience of having more control and more time to carry them out. It is also noted that the degree of cerebellar involvement is associated with the complexity of learning that is required and once the skill has been acquired this cerebellar contribution reduces. Such changes are especially evident when learning new skills such as yoga, golf and surfing, with patients often spontaneously reporting an enhancement of their coordination. Of particular mention was the improved ability to engage in team sports which had been difficult due the dual focus to attend to individual skills and the role within the team. As the skills were rarely automatic the ability to simultaneously master both activities did not occur, however on the combination of treatments a significant benefit was noted.
3. Eye tracking also appear to have a component of cerebellar control, which ties in with saccadic eye movements.

The cerebellum is a region of the brain that plays an important role in the integration of sensory perception and motor output. Many neural pathways link the cerebellum with the motor cortex—which sends information to the muscles causing them to move—and the spinocerebellar tract—which provides feedback on the position of the body in space (proprioception). The cerebellum integrates these pathways, using the constant feedback on body position to fine-tune motor movements. Because of this 'updating' function of the cerebellum, lesions within it are not so debilitating as to cause paralysis, but rather present as feedback deficits resulting in disorders in fine movement, equilibrium, posture, and motor learning.

The deficiencies present in the patients prior to treatment may therefore be at least in part a result of defects in cerebellar function. These deficiencies can be referred to as motor planning and sequencing deficiencies, which describes both the language and movement aspect of the condition. Thus since the cerebellum is involved in the automation of skills, the effects of the medication on cerebellar function assist in the acquisition of new skills.

Finally, the verbal and reading fluency of the patients improves with treatment using the anti-epileptic mood stabilisers.

Whilst pyschostimulants alone do have some impact on the above, but only with some effort which in time fatigues, the benefit of the anti-epileptic mood stabilisers is that they allow more effortless and therefore sustainable function.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. A method of treating Autistic Spectrum Disorder in an individual suffering from said disorder, but not epilepsy or bipolar disorder, the method consisting essentially of administering to the individual phenytoin at a dose of less than 60 mg per day, to thereby treat Autistic Spectrum Disorder in said individual.

2. The method according to claim 1, wherein the individual suffers from learning difficulties.

* * * * *